(12) United States Patent
Ritland

(10) Patent No.: US 7,455,639 B2
(45) Date of Patent: Nov. 25, 2008

(54) OPPOSING PARALLEL BLADED RETRACTOR AND METHOD OF USE

(76) Inventor: Stephen Ritland, 1150 N. San Francisco St., Flagstaff, AZ (US) 86001

( * ) Notice: Subject to any disclaimer, the term of this patent is extended or adjusted under 35 U.S.C. 154(b) by 287 days.

(21) Appl. No.: 11/228,106

(22) Filed: Sep. 16, 2005

(65) Prior Publication Data
US 2006/0063978 A1    Mar. 23, 2006

Related U.S. Application Data

(60) Provisional application No. 60/611,836, filed on Sep. 20, 2004.

(51) Int. Cl.
*A61B 1/32* (2006.01)
(52) U.S. Cl. .................. 600/219; 600/201; 600/213
(58) Field of Classification Search .................. 285/51; 600/123, 201, 213, 219, 220, 225, 244; 604/902; 403/76, 114, 115
See application file for complete search history.

(56) References Cited

U.S. PATENT DOCUMENTS

| | | | |
|---|---|---|---|
| 2,191 A | 7/1841 | Pitney |
| 569,839 A | 10/1896 | Roeloffs |
| 605,652 A | 6/1898 | Pitt |
| 1,090,746 A | 3/1914 | Nourse |
| 1,097,978 A | 5/1914 | Johnson |
| 3,467,079 A | 9/1969 | James |
| 3,470,872 A | 10/1969 | Grieshaber |
| 3,875,595 A | 4/1975 | Froning |
| 3,893,454 A | 7/1975 | Hagelin |
| 4,041,939 A | 8/1977 | Hall |
| 4,232,660 A | 11/1980 | Coles |
| 4,440,168 A | 4/1984 | Warren |
| 4,481,947 A | 11/1984 | Chester |
| 4,545,374 A | 10/1985 | Jacobson |
| 4,573,448 A | 3/1986 | Kambin |
| 4,617,922 A | 10/1986 | Griggs |
| 4,620,460 A | 11/1986 | Gonzales, Jr. |
| 4,686,972 A | 8/1987 | Kurland |
| 4,736,738 A | 4/1988 | Lipovsek |
| 4,743,260 A | 5/1988 | Burton |
| 4,747,394 A | 5/1988 | Watanabe |

(Continued)

FOREIGN PATENT DOCUMENTS

EP    0820731    5/2003

(Continued)

OTHER PUBLICATIONS

U.S. Appl. No. 10/165,991, Simonson.

(Continued)

*Primary Examiner*—Cris L Rodriguez
*Assistant Examiner*—Hao D Mai
(74) *Attorney, Agent, or Firm*—Holme Roberts Owen LLP

(57) ABSTRACT

A retractor is provided for maintaining substantially parallel blade alignment with the longitudinal axis of the retractor during opening and closing the retractor blades. The retractor includes rotatable blade receptacles and hinged blade arms interconnected to rotatable arms for maintaining the alignment of the blades during opening and closing. In addition, the retractor may include interchangeable blades, means for locking the blade position, and means for securing the retractor to a mechanical arm.

14 Claims, 3 Drawing Sheets

U.S. PATENT DOCUMENTS

| | | | |
|---|---|---|---|
| 4,798,111 A | 1/1989 | Cheeseman | |
| 4,803,976 A | 2/1989 | Frigg | |
| 4,817,587 A | 4/1989 | Janese | |
| 4,862,891 A | 9/1989 | Smith | |
| 4,863,423 A | 9/1989 | Wallace | |
| 4,882,958 A | 11/1989 | McNeely | |
| 4,889,112 A | 12/1989 | Schachner et al. | |
| 4,974,985 A * | 12/1990 | Glatzel | 403/114 |
| 4,995,875 A | 2/1991 | Coes | |
| 5,002,542 A | 3/1991 | Frigg | |
| 5,002,576 A | 3/1991 | Fuhrmann et al. | |
| 5,018,507 A | 5/1991 | Montaldi | |
| 5,026,373 A | 6/1991 | Ray et al. | |
| 5,030,220 A | 7/1991 | Howland | |
| 5,030,223 A | 7/1991 | Anderson et al. | |
| 5,035,232 A | 7/1991 | Lutze et al. | |
| 5,048,379 A | 9/1991 | Gramera | |
| 5,052,373 A | 10/1991 | Michelson | |
| 5,055,104 A | 10/1991 | Ray | |
| 5,084,043 A | 1/1992 | Hertzmann | |
| 5,098,435 A | 3/1992 | Stednitz | |
| 5,106,376 A | 4/1992 | Mononen | |
| 5,129,900 A | 7/1992 | Asher et al. | |
| 5,133,720 A | 7/1992 | Greenberg | |
| 5,135,525 A | 8/1992 | Biscoping | |
| 5,148,724 A | 9/1992 | Rexford | |
| 5,158,543 A | 10/1992 | Lazarus | |
| 5,165,306 A * | 11/1992 | Hellon | 74/588 |
| 5,195,541 A | 3/1993 | Obenchain | |
| 5,217,007 A | 6/1993 | Ciaglia | |
| 5,275,600 A | 1/1994 | Allard et al. | |
| 5,275,611 A | 1/1994 | Behl | |
| 5,279,567 A | 1/1994 | Ciaglia | |
| 5,292,309 A | 3/1994 | Van Tassel | |
| 5,303,694 A | 4/1994 | Mikhail | |
| 5,306,275 A | 4/1994 | Bryan | |
| 5,306,309 A | 4/1994 | Wagner et al. | |
| 5,312,360 A | 5/1994 | Behl | |
| 5,312,405 A | 5/1994 | Korotko et al. | |
| 5,330,474 A | 7/1994 | Lin | |
| 5,356,413 A | 10/1994 | Martins et al. | |
| 5,363,841 A | 11/1994 | Coker | |
| 5,415,661 A | 5/1995 | Holmes | |
| 5,431,639 A | 7/1995 | Shaw | |
| 5,431,651 A | 7/1995 | Goble | |
| D361,381 S | 8/1995 | Koros et al. | |
| 5,439,464 A | 8/1995 | Shapiro | |
| 5,466,238 A | 11/1995 | Lin | |
| 5,472,426 A | 12/1995 | Bonati | |
| 5,474,555 A | 12/1995 | Puno et al. | |
| 5,484,440 A | 1/1996 | Allard | |
| 5,489,274 A | 2/1996 | Chu | |
| 5,489,308 A | 2/1996 | Kuslich et al. | |
| 5,498,262 A | 3/1996 | Bryan | |
| 5,499,983 A | 3/1996 | Hughes | |
| 5,501,684 A | 3/1996 | Schlapfer et al. | |
| 5,512,038 A | 4/1996 | O'Neal et al. | |
| 5,558,622 A | 9/1996 | Greenberg | |
| 5,565,502 A | 10/1996 | Glimcher et al. | |
| 5,569,300 A | 10/1996 | Redmon | |
| 5,584,833 A | 12/1996 | Fournet-Fayard et al. | |
| 5,591,166 A | 1/1997 | Bernhardt et al. | |
| 5,591,235 A | 1/1997 | Kuslich | |
| 5,593,409 A | 1/1997 | Michelson | |
| 5,601,550 A | 2/1997 | Esser | |
| 5,603,714 A | 2/1997 | Kaneda et al. | |
| 5,611,778 A | 3/1997 | Brinon | |
| 5,628,740 A | 5/1997 | Mullane | |
| 5,643,263 A | 7/1997 | Simonson | |
| 5,643,264 A | 7/1997 | Sherman et al. | |
| 5,645,544 A | 7/1997 | Tai et al. | |
| 5,645,599 A | 7/1997 | Samani | |
| 5,683,392 A | 11/1997 | Richelsoph et al. | |
| 5,683,463 A | 11/1997 | Godefroy et al. | |
| 5,687,739 A | 11/1997 | McPherson | |
| 5,690,632 A | 11/1997 | Schwartz et al. | |
| 5,691,397 A | 11/1997 | Glimcher et al. | |
| 5,702,455 A | 12/1997 | Saggar | |
| 5,716,355 A | 2/1998 | Jackson et al. | |
| 5,716,415 A | 2/1998 | Steffee | |
| 5,725,528 A | 3/1998 | Errico et al. | |
| 5,735,850 A | 4/1998 | Baumgartner et al. | |
| 5,735,851 A | 4/1998 | Errico et al. | |
| 5,735,899 A | 4/1998 | Schwartz et al. | |
| 5,743,853 A | 4/1998 | Lauderdale | |
| 5,746,720 A | 5/1998 | Stouder, Jr. | |
| 5,746,741 A | 5/1998 | Kraus et al. | |
| 5,752,957 A | 5/1998 | Ralph et al. | |
| 5,766,221 A | 6/1998 | Benderev et al. | |
| 5,766,253 A | 6/1998 | Brosnahan, III | |
| 5,772,582 A | 6/1998 | Huttner et al. | |
| 5,782,832 A | 7/1998 | Larsen et al. | |
| 5,785,648 A | 7/1998 | Min | |
| 5,785,710 A | 7/1998 | Michelson | |
| 5,785,712 A | 7/1998 | Runciman et al. | |
| 5,792,044 A | 8/1998 | Foley | |
| 5,797,912 A | 8/1998 | Runciman et al. | |
| 5,800,435 A | 9/1998 | Errico et al. | |
| 5,810,816 A | 9/1998 | Roussouly et al. | |
| 5,810,817 A | 9/1998 | Roussouly et al. | |
| D399,955 S | 10/1998 | Koros et al. | |
| 5,816,257 A | 10/1998 | Chin | |
| 5,827,328 A | 10/1998 | Buttermann | |
| 5,836,948 A | 11/1998 | Zucherman et al. | |
| RE36,020 E | 12/1998 | Moore et al. | |
| 5,851,207 A | 12/1998 | Cesarone | |
| 5,860,977 A | 1/1999 | Zucherman et al. | |
| 5,865,847 A | 2/1999 | Kohrs et al. | |
| 5,865,848 A | 2/1999 | Baker | |
| 5,876,404 A | 3/1999 | Zucherman et al. | |
| 5,882,344 A | 3/1999 | Stouder, Jr. | |
| 5,885,285 A | 3/1999 | Simonson | |
| 5,885,299 A | 3/1999 | Winslow et al. | |
| 5,885,300 A | 3/1999 | Tokuhashi et al. | |
| 5,891,147 A | 4/1999 | Moskovitz et al. | |
| 5,895,352 A | 4/1999 | Kleiner | |
| 5,895,390 A | 4/1999 | Moran et al. | |
| 5,897,593 A | 4/1999 | Kohrs et al. | |
| 5,899,901 A | 5/1999 | Middleton | |
| 5,902,231 A | 5/1999 | Foley | |
| 5,902,304 A | 5/1999 | Walker et al. | |
| 5,904,650 A * | 5/1999 | Wells | 600/226 |
| 5,906,616 A | 5/1999 | Pavlov et al. | |
| 5,913,818 A | 6/1999 | Co et al. | |
| 5,928,139 A | 7/1999 | Koros | |
| 5,928,233 A | 7/1999 | Apfelbaum et al. | |
| 5,938,663 A | 8/1999 | Petreto | |
| 5,944,658 A | 8/1999 | Koros et al. | |
| 5,947,965 A | 9/1999 | Bryan | |
| 5,954,635 A | 9/1999 | Foley | |
| 5,954,671 A | 9/1999 | O'Neil | |
| 5,961,516 A | 10/1999 | Graf | |
| 5,967,970 A | 10/1999 | Cowan | |
| 5,968,098 A | 10/1999 | Winslow | |
| 5,971,920 A | 10/1999 | Nagel | |
| 5,976,135 A | 11/1999 | Sherman et al. | |
| 5,976,146 A | 11/1999 | Ogawa | |
| 5,984,924 A | 11/1999 | Asher et al. | |
| 5,996,447 A | 12/1999 | Bayouth | |
| 5,997,539 A | 12/1999 | Errico et al. | |
| 6,004,322 A | 12/1999 | Bernstein | |
| 6,007,487 A | 12/1999 | Foley et al. | |
| 6,010,520 A | 1/2000 | Pattison | |
| 6,017,342 A * | 1/2000 | Rinner | 606/57 |

| | | | |
|---|---|---|---|
| 6,027,533 A | 2/2000 | Olerud |
| 6,045,579 A | 4/2000 | Hochshuler et al. |
| 6,048,342 A | 4/2000 | Zucherman et al. |
| 6,050,997 A | 4/2000 | Mullane |
| 6,063,088 A | 5/2000 | Winslow |
| 6,068,630 A | 5/2000 | Zucherman et al. |
| 6,074,390 A | 6/2000 | Zucherman et al. |
| 6,074,393 A | 6/2000 | Sitoto |
| 6,080,155 A | 6/2000 | Michelson |
| 6,080,193 A | 6/2000 | Hochshuler et al. |
| 6,081,741 A | 6/2000 | Hollis |
| 6,083,225 A | 7/2000 | Winslow et al. |
| 6,090,112 A | 7/2000 | Zucherman et al. |
| 6,102,948 A | 8/2000 | Brosnahan, III |
| 6,113,602 A | 9/2000 | Sand |
| 6,117,137 A | 9/2000 | Halm et al. |
| 6,117,174 A | 9/2000 | Nolan |
| 6,120,434 A | 9/2000 | Kimura |
| 6,120,506 A | 9/2000 | Kohrs et al. |
| 6,123,705 A | 9/2000 | Michelson |
| 6,123,706 A | 9/2000 | Lange |
| 6,132,430 A | 10/2000 | Wagner |
| D433,296 S | 11/2000 | Yamakawa |
| 6,146,383 A | 11/2000 | Studer et al. |
| 6,149,652 A | 11/2000 | Zucherman et al. |
| 6,149,686 A | 11/2000 | Kuslich et al. |
| 6,152,871 A | 11/2000 | Foley |
| 6,152,926 A | 11/2000 | Zucherman et al. |
| 6,156,006 A | 12/2000 | Brosens |
| 6,156,038 A | 12/2000 | Zucherman et al. |
| 6,159,179 A | 12/2000 | Simonson |
| 6,162,170 A | 12/2000 | Foley |
| 6,162,236 A | 12/2000 | Osada |
| D436,513 S | 1/2001 | Yamakawa |
| 6,176,823 B1 | 1/2001 | Foley |
| 6,176,861 B1 | 1/2001 | Bernstein et al. |
| 6,179,838 B1 | 1/2001 | Fiz |
| D438,074 S | 2/2001 | Marr |
| 6,183,471 B1 | 2/2001 | Zucherman et al. |
| 6,187,005 B1 | 2/2001 | Brace et al. |
| 6,190,387 B1 | 2/2001 | Zucherman et al. |
| 6,190,414 B1 | 2/2001 | Young et al. |
| 6,196,969 B1 * | 3/2001 | Bester et al. ............... 600/224 |
| 6,197,002 B1 | 3/2001 | Peterson |
| 6,206,822 B1 | 3/2001 | Foley |
| 6,206,826 B1 | 3/2001 | Mathews et al. |
| 6,206,885 B1 | 3/2001 | Ghahremani et al. |
| 6,206,922 B1 | 3/2001 | Zdeblick et al. |
| 6,206,923 B1 | 3/2001 | Boyd et al. |
| 6,210,413 B1 | 4/2001 | Justis et al. |
| 6,214,004 B1 | 4/2001 | Coker |
| 6,217,509 B1 | 4/2001 | Foley |
| 6,224,597 B1 | 5/2001 | Coker |
| 6,224,608 B1 | 5/2001 | Ciccolella |
| 6,224,631 B1 | 5/2001 | Kohrs |
| 6,231,575 B1 | 5/2001 | Krag |
| 6,235,030 B1 | 5/2001 | Zucherman et al. |
| 6,238,397 B1 | 5/2001 | Zucherman et al. |
| 6,245,072 B1 | 6/2001 | Zdeblick et al. |
| 6,248,104 B1 | 6/2001 | Chopin et al. |
| 6,248,106 B1 | 6/2001 | Ferree |
| 6,258,097 B1 | 7/2001 | Cook |
| 6,261,287 B1 | 7/2001 | Metz-Stavenhagen |
| 6,264,658 B1 | 7/2001 | Lee et al. |
| 6,267,763 B1 | 7/2001 | Castro |
| 6,267,764 B1 | 7/2001 | Elberg |
| 6,267,765 B1 | 7/2001 | Taylor et al. |
| 6,270,498 B1 | 8/2001 | Michelson |
| 6,273,914 B1 | 8/2001 | Papas |
| 6,283,966 B1 | 9/2001 | Houfburg |
| 6,287,309 B1 | 9/2001 | Baccelli et al. |
| 6,287,313 B1 | 9/2001 | Sasso |
| 6,287,343 B1 | 9/2001 | Kuslich et al. |
| 6,290,700 B1 | 9/2001 | Schmotzer |
| 6,293,949 B1 | 9/2001 | Justis et al. |
| 6,296,609 B1 | 10/2001 | Brau |
| 6,299,614 B1 | 10/2001 | Kretschmer et al. |
| 6,302,842 B1 | 10/2001 | Auerbach et al. |
| 6,309,390 B1 | 10/2001 | Le Couedic et al. |
| 6,309,391 B1 | 10/2001 | Crandall et al. |
| 6,312,432 B1 | 11/2001 | Leppelmeier |
| 6,332,883 B1 | 12/2001 | Zucherman et al. |
| 6,342,057 B1 | 1/2002 | Brace |
| 6,348,058 B1 | 2/2002 | Melkent et al. |
| 6,354,176 B1 | 3/2002 | Nordlin |
| 6,355,038 B1 | 3/2002 | Pisharodi |
| 6,361,541 B1 | 3/2002 | Barnhart |
| 6,368,350 B1 | 4/2002 | Erickson et al. |
| 6,368,351 B1 | 4/2002 | Glenn et al. |
| 6,371,959 B1 | 4/2002 | Trice |
| 6,371,968 B1 | 4/2002 | Kogasaka |
| 6,391,058 B1 | 5/2002 | Kuslich et al. |
| 6,395,033 B1 | 5/2002 | Pepper |
| 6,418,821 B1 | 7/2002 | Yamakawa |
| 6,425,901 B1 | 7/2002 | Zhu et al. |
| 6,428,472 B1 | 8/2002 | Haas |
| 6,440,169 B1 | 8/2002 | Elberg et al. |
| 6,443,953 B1 | 9/2002 | Perra et al. |
| 6,443,989 B1 | 9/2002 | Jackson |
| 6,461,330 B1 | 10/2002 | Miyagi |
| 6,461,359 B1 | 10/2002 | Tribus et al. |
| 6,478,798 B1 | 11/2002 | Howland |
| D466,766 S | 12/2002 | Marty |
| 6,520,907 B1 | 2/2003 | Foley |
| 6,524,238 B2 | 2/2003 | Velikaris et al. |
| 6,530,926 B1 | 3/2003 | Davison |
| 6,540,756 B1 | 4/2003 | Vaughan |
| 6,551,320 B2 | 4/2003 | Lieberman |
| 6,554,831 B1 | 4/2003 | Rivard et al. |
| 6,565,569 B1 | 5/2003 | Assaker et al. |
| 6,569,164 B1 | 5/2003 | Assaker et al. |
| 6,579,292 B2 | 6/2003 | Taylor |
| 6,585,738 B1 | 7/2003 | Mangione et al. |
| 6,595,993 B2 | 7/2003 | Donno et al. |
| 6,610,062 B2 | 8/2003 | Bailey et al. |
| 6,626,904 B1 | 9/2003 | Jammet et al. |
| 6,626,906 B1 | 9/2003 | Young |
| 6,648,887 B2 | 11/2003 | Ashman |
| 6,671,725 B1 | 12/2003 | Noel et al. |
| 6,676,661 B1 | 1/2004 | Martin Benlloch et al. |
| 6,682,532 B2 | 1/2004 | Johnson et al. |
| 6,685,705 B1 | 2/2004 | Taylor |
| 6,692,434 B2 | 2/2004 | Ritland |
| 6,736,816 B2 | 5/2004 | Ritland |
| 6,743,257 B2 | 6/2004 | Castro |
| 6,749,613 B1 | 6/2004 | Conchy et al. |
| 6,761,719 B2 | 7/2004 | Justis et al. |
| 6,783,528 B2 | 8/2004 | Vincent-Prestigiacomo |
| 6,929,606 B2 | 8/2005 | Ritland |
| 6,951,538 B2 | 10/2005 | Ritland |
| 6,955,678 B2 | 10/2005 | Gabriel et al. |
| 6,974,480 B2 | 12/2005 | Messerli et al. |
| 6,991,632 B2 | 1/2006 | Ritland |
| 2001/0005796 A1 | 6/2001 | Zdeblick et al. |
| 2001/0010021 A1 | 7/2001 | Boyd et al. |
| 2001/0012942 A1 | 8/2001 | Estes |
| 2001/0027320 A1 | 10/2001 | Sasso |
| 2001/0047207 A1 | 11/2001 | Michelson |
| 2002/0011135 A1 | 1/2002 | Hall |
| 2002/0016592 A1 | 2/2002 | Branch |
| 2002/0022764 A1 | 2/2002 | Smith |
| 2002/0029082 A1 | 3/2002 | Muhanna |
| 2002/0049368 A1 | 4/2002 | Ritland |
| 2002/0058948 A1 | 5/2002 | Arlettaz |
| 2002/0068973 A1 | 6/2002 | Jackson |
| 2002/0068975 A1 | 6/2002 | Teitelbaum et al. |

| | | | |
|---|---|---|---|
| 2002/0077632 A1 | 6/2002 | Tsou | |
| 2002/0082695 A1 | 6/2002 | Neumann | |
| 2002/0107571 A1 | 8/2002 | Foley | |
| 2002/0107572 A1 | 8/2002 | Foley et al. | |
| 2002/0120270 A1 | 8/2002 | Trieu et al. | |
| 2002/0123668 A1 | 9/2002 | Ritland | |
| 2002/0143235 A1 | 10/2002 | Pagliuca | |
| 2003/0083686 A1 | 5/2003 | Simonson | |
| 2003/0083689 A1 | 5/2003 | Simonson | |
| 2003/0093078 A1 | 5/2003 | Ritland | |
| 2003/0109880 A1 | 6/2003 | Shirado et al. | |
| 2003/0139812 A1 | 7/2003 | Garcia et al. | |
| 2003/0144665 A1 | 7/2003 | Munting | |
| 2003/0171749 A1 | 9/2003 | Le Couedic et al. | |
| 2003/0171751 A1 | 9/2003 | Ritland | |
| 2003/0187431 A1 | 10/2003 | Simonson | |
| 2003/0191470 A1 | 10/2003 | Ritland | |
| 2003/0220689 A1 | 11/2003 | Ritland | |
| 2003/0236447 A1 | 12/2003 | Ritland | |
| 2004/0002708 A1 | 1/2004 | Ritland | |
| 2004/0106997 A1 | 6/2004 | Lieberson | |
| 2004/0138534 A1 | 7/2004 | Ritland | |
| 2004/0172023 A1 | 9/2004 | Ritland | |
| 2004/0181223 A1 | 9/2004 | Ritland | |
| 2004/0254428 A1 | 12/2004 | Ritland | |
| 2005/0004593 A1 | 1/2005 | Simonson | |
| 2005/0020920 A1 | 1/2005 | Ritland | |
| 2005/0027360 A1 | 2/2005 | Webb et al. | |
| 2005/0143737 A1 | 6/2005 | Paffard et al. | |
| 2005/0149023 A1 | 7/2005 | Ritland | |
| 2005/0149191 A1 | 7/2005 | Cragg et al. | |
| 2005/0203517 A1 | 9/2005 | Jahng et al. | |
| 2005/0203519 A1 | 9/2005 | Harms et al. | |
| 2005/0209694 A1 | 9/2005 | Loeb | |
| 2005/0228233 A1 | 10/2005 | Ritland | |
| 2006/0009768 A1 | 1/2006 | Ritland | |
| 2006/0041259 A1 | 2/2006 | Paul et al. | |
| 2006/0064090 A1 | 3/2006 | Park | |
| 2006/0069390 A1 | 3/2006 | Frigg et al. | |

FOREIGN PATENT DOCUMENTS

| | | |
|---|---|---|
| FR | 2796828 | 2/2001 |
| WO | WO 99/40866 | 8/1999 |
| WO | WO 00/18306 | 4/2000 |
| WO | WO 02/02022 | 1/2002 |
| WO | WO 02/07621 | 1/2002 |
| WO | WO 02/060330 | 8/2002 |
| WO | WO 03/026523 | 4/2003 |
| WO | WO 03/073908 | 9/2003 |
| WO | WO 03/094699 | 11/2003 |
| WO | WO 2004/075778 | 9/2004 |
| WO | WO 2004/089244 | 10/2004 |

OTHER PUBLICATIONS

U.S. Appl. No. 11/425,987, Ritland.
China Chemical Reporter, "Rapid Development of Polyether Ether Ketone", CNCIC Chemdata Inc., 2004, 2 pages.
Green, "Body Building—Medical Materials for Systems and Scaffolding," Materials World, Journal of the Institute of Materials, vol. 10, No. 2, 2001, 4 pages.
Green, "Effects of Gamma Sterilisation on Implant Grade Polyetheretherketone," Invibio Inc., Lancashire, United Kingdom, undated, 1 page.
Green, "In Vivo Biostability Study on Polyaryletheretherketone Biomaterial," Invibio Inc., Lancashire, United Kingdom, undated, 2 pages.
Green, et al., "A Polyaryletherketone Biomaterial for Use in Medical Implant Applications," Lancashire, United Kingdom, 2001, 1 page.
Green, et al., "Polyetheretherketone Polymer and Compounds for Surgical Applications," Lancashire, United Kingdom, undated, 9 pages.
Green, Stuart, "PEEK-Optima Polymer in the Implantable Medical Device Industry," Invibio Inc., Lancashire, United Kingdom, undated, 2 pages.
Invibio, Biomaterials Solutions, "High Performance PEEK-Optima Biocompatible Polymer Chosen for Dental Abutment Healing Caps," Invibio Inc., Lancashire, United Kingdom, undated, 1 page.
Invibio, Biomaterials Solutions, "High Performance PEEK-Optima Biocompatible Polymer Chosen for New Generation Heart Valve," Invibio Inc., Lancashire, United Kingdom, undated, 1 page.
Invibio, Biomaterials Solutions, "PEEK-Classix," Invibio Inc., Lancashire, United Kingdom, 2003, 2 pages.
Invibio, Biomaterials Solutions, "PEEK-Optima Polymer: Performance Purity Flexibility Endurance," Invibio Inc., Lancashire, United Kingdom, 2004, 3 pages.
Invibio, Biomaterials Solutions, "PEEK-Optima, Composite Hip," Invibio Inc., Lancashire, United Kingdom, undated, 2 pages.
Invibio, Biomaterials Solutions, "PEEK-Optima, Spiked Washers," Invibio Inc., Lancashire, United Kingdom, undated, 1 page.
Sofamor Danek Video Systems Brochure.
Tangram Technology Ltd., "Polymer Data File: Polyether Ether Keotone-PEEK," Available at http://www.tangram.co.uk/TI-Polymer-PEEK.html, 2001, 5 pages.
Web pages, http://www.brainlab.com, Apr. 2, 2002; 5 pp.
"New Minimally Invasive Techniques, Improve Outcome of Spine Surgeries", Medtronic Sofamor Danek.
Caspar; "Technique of Microsurgery: Microsurgery of the Lumbar Spine: Principles and Techniques in Spine Surgery"; *Aspen Publications*; 1990; 105-122.
Hilton et al.; "Meditronic Sofamor Danek METRX Microdiscectomy Surgical Technique Brochure"; 2000.
Kambin; "Arthroscopic Microdiscectomy: Minimal Intervention in Spinal Surgery"; *National Library of Medicine*; 1991; 67-100.
Kambin; "Percutaneous Posterolateral Discectomy"; *Clincial Orthopaedics and Related Research, Section II*; 145-154119.
Savitz; "Same-Day Microsurgical Arthroscopic Latera-Approach Laser-Assisted (SMALL) Fluoroscopic Discectomy"; *Journal of Neurosurgery*; Jun. 1994; 1039-1045.
Schaffer et al.; "Percutaneous Posterolateral Lumbar Discectomy and Decompression with a 6.9 Millimeter Cannula"; *Journal of Bone and Joint Surgery*; 1991; 822-831.
Wiltse; "New Uses and Refinements of the Paraspinal Approach to the Lumbar Spine"; *Spine*, vol. 13 No. 6 1988, p. 696-706.

* cited by examiner

OPPOSING PARALLEL BLADED RETRACTOR AND METHOD OF USE

CROSS-REFERENCE TO RELATED APPLICATIONS

Priority is claimed from U.S. Provisional Patent Application No. 60/611,836 filed Sep. 20, 2004 entitled "Opposing Parallel Bladed Retractor and Method of Use," which is incorporated herein by reference in its entirety.

FIELD OF THE INVENTION

The present invention is directed to retractor for use in surgical procedures, and methods of use for the retractor.

BACKGROUND OF THE INVENTION

Many existing retractors for surgical procedures utilize a single blade. For those instances where more than one blade is used, the retractors often have a configuration that is difficult to manipulate, and/or wherein the blades, when separated to displace tissue, are spread apart in an arcuate fashion, such that the blades are no longer parallel with the longitudinal axis of the retractor after the retractor is opened. In addition, retractors fail to include a locking mechanism, and cannot be readily interconnected to a mechanical arm to hold the position of the retractor.

Existing retractors with interchangeable blades typically place the connection with the interchangeable blade at the top of the blade. In addition, existing retractors with interchangeable blades have blades that clip on with the bulk of the retractor located on either side of the surgical wound instead of away from it. If during a spinal surgery a surgeon has a retractor in place and the pedicle screws have already been inserted into one or more vertebra during the surgery, and the surgeon then desires to subsequently tighten the pedicle screws, then if a bulky retractor is in place, the surgeon cannot readily access the screws. Accordingly, there is a need for a surgical retractor with interchangeable blades that places the bulk of the retractor away from the surgical wound.

SUMMARY OF THE INVENTION

The present invention solves the above mention deficiencies by providing a retractor that allows a surgeon to displace the tissue in the area of the target surgical site while maintaining a blade alignment that is substantially parallel to the longitudinal axis of the retractor. The blades may be slidably positioned within the blade receptacles of the retractor for use. In addition, the blades may be removed and interchanged during a surgical procedure.

The present invention preferably includes a pair of blade receptacles that are pivotably interconnected to the blade arms of the retractor. In addition, the blade receptacles are preferably pivotably interconnected to rotatable members that, in turn, are pivotably interconnected to a central arm of the retractor.

In a separate aspect of the invention, means for selectively securing the position of the blades is provided.

In yet a separate aspect of the invention, means for securing the retractor to a mechanical arm is provided.

Various embodiments of the present invention are set forth in the attached figures and in the detailed description of the invention as provided herein and as embodied by the claims. It should be understood, however, that this Summary of the Invention may not contain all of the aspects and embodiments of the present invention, is not meant to be limiting or restrictive in any manner, and that the invention as disclosed herein is and will be understood by those of ordinary skill in the art to encompass obvious improvements and modifications thereto.

Additional advantages of the present invention will become readily apparent from the following discussion, particularly when taken together with the accompanying drawings.

BRIEF DESCRIPTION OF THE DRAWINGS

FIG. 1A is a detailed cross-sectional view of the closed blades of FIG. 1 taken along line IA-IA of FIG. 1;

FIG. 2A is a detailed cross-sectional view of a blade receptacle taken along line 2A-2A of FIG. 2.

DETAILED DESCRIPTION OF THE INVENTION

Figure 1:
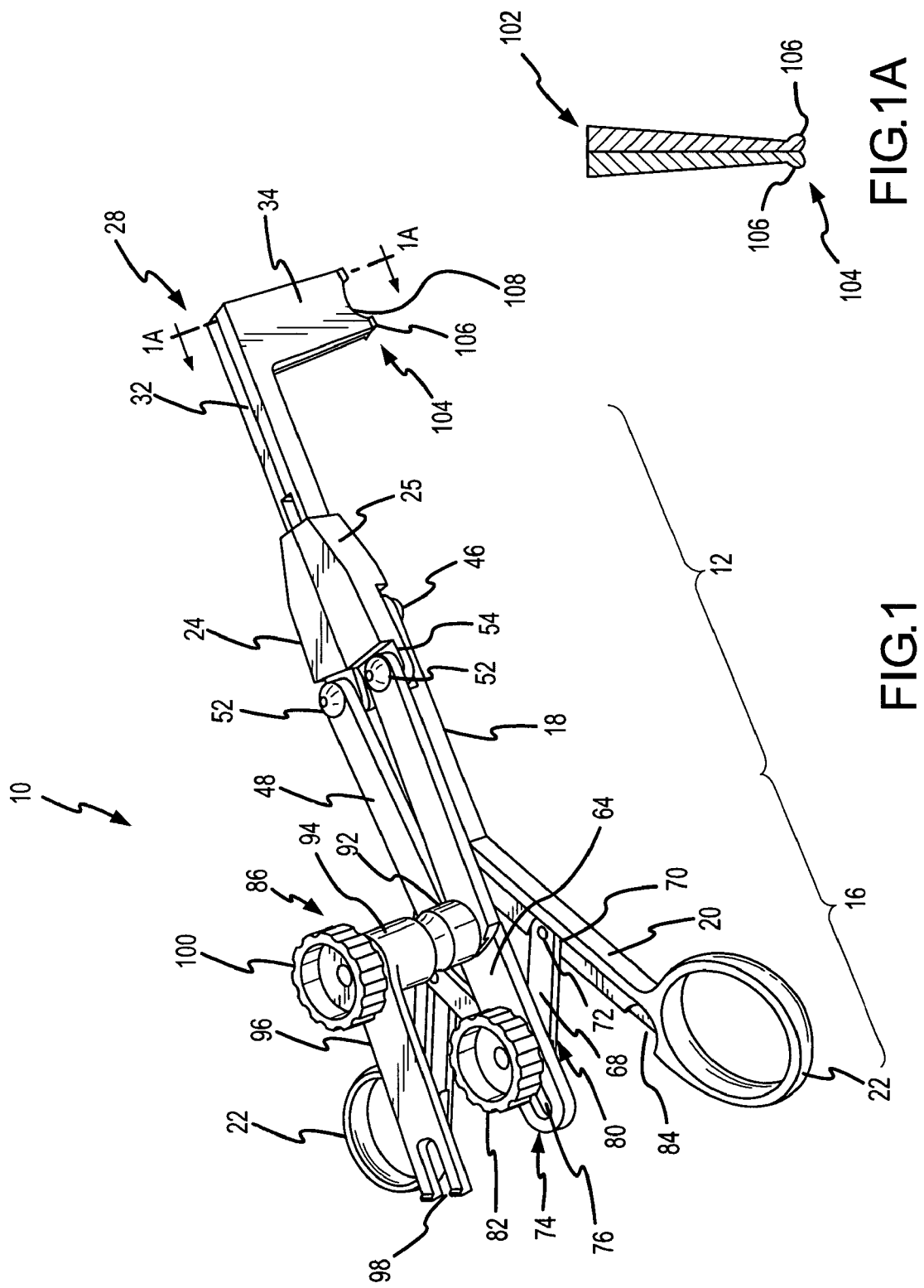
FIG. 1 is a perspective view of a first embodiment of the retractor of the present invention, wherein the blades of the retractor are in a closed position.
Figure 2:
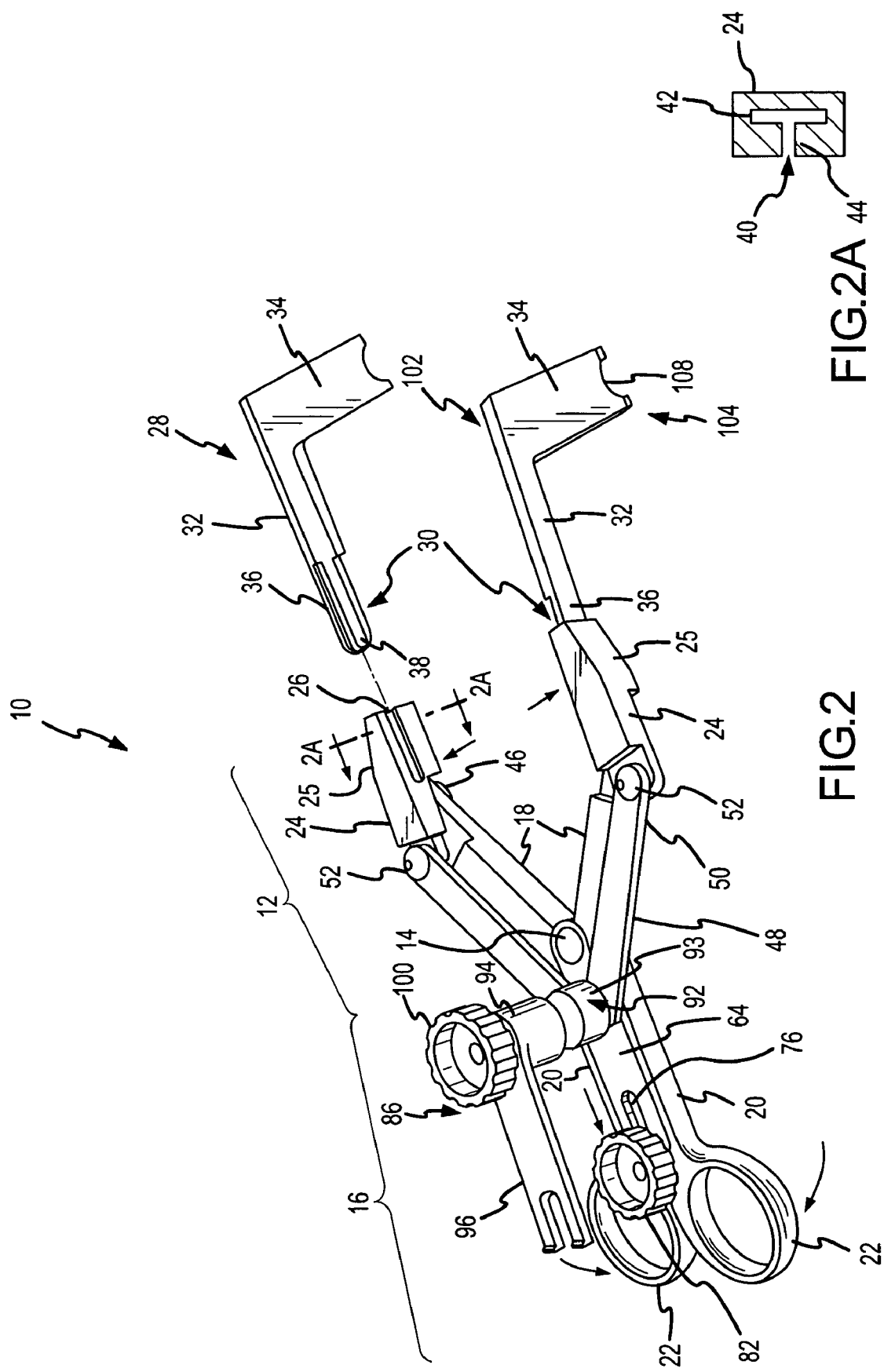
FIG. 2 is a perspective view of the retractor of FIG. 1, wherein the blades of the retractor are in an open position, and wherein one of the blades is slidably removed from the retractor.
Figure 3:
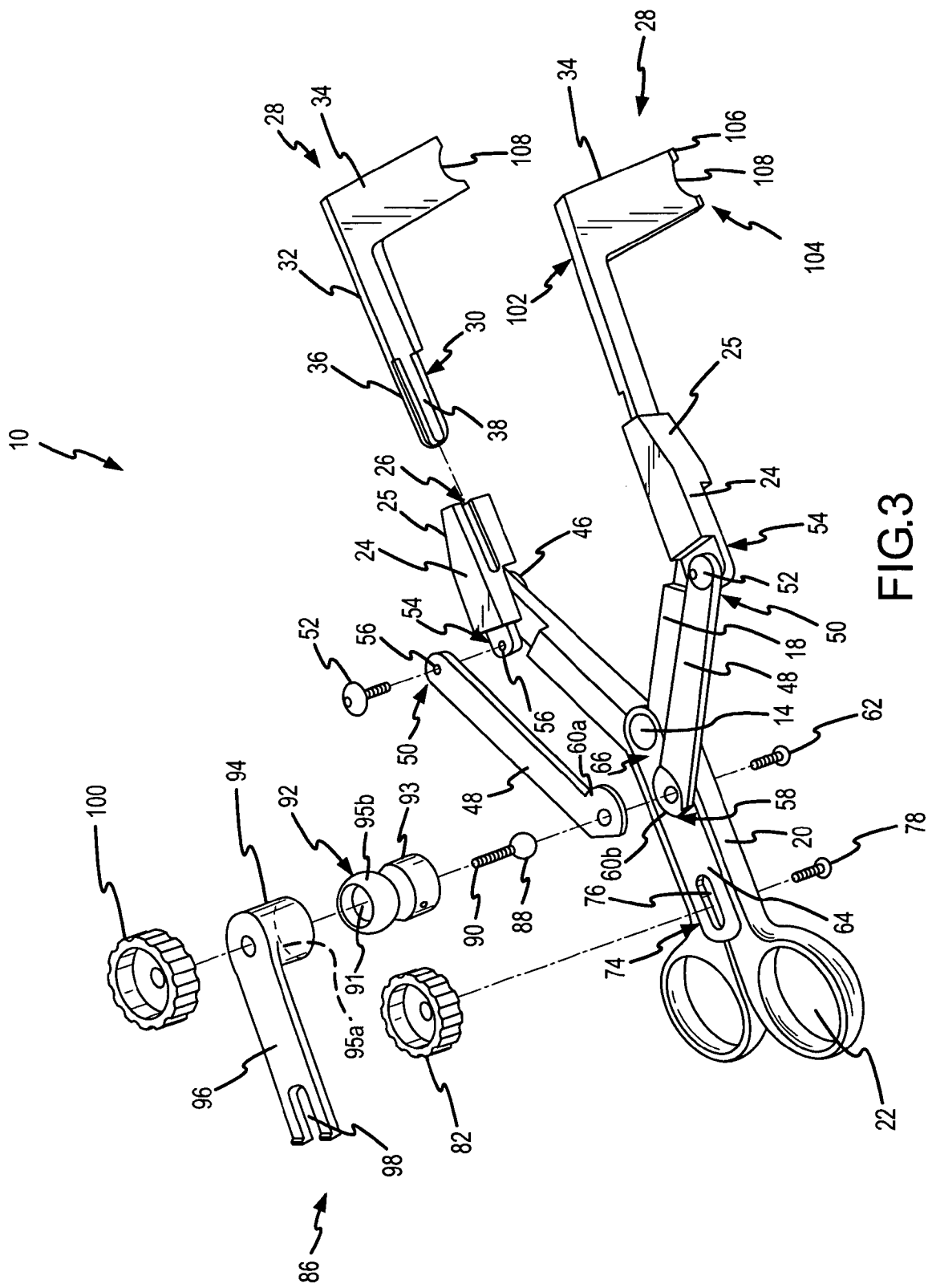
FIG. 3 is a partially exploded perspective view of the retractor shown in FIG. 2.

Referring now to FIGS. 1-3, a retractor apparatus constructed in accordance with an embodiment of the present invention is generally identified by reference numeral 10. Retractor 10 includes a front portion 12, a central hinge 14, and a rear or handle portion 16. The front portion 12 preferably includes opposing blade arms 18 that are interconnected to the blades as discussed below. The handle portion 16 preferably includes opposing handle arms 20. The handle arms 20 preferably include a contoured grip or handle opening 22 for a person, such as a surgeon, to grasp and manipulate the retractor 10.

Interconnected to the blade arms 18 of the front portion 12 are the blade receptacles 24. The blade receptacles 24 preferably include slots 26 for receiving blades 28. More particularly, one aspect of the present invention is to provide insertable and/or removable blades 28, wherein the blades 28 can be interchanged into the blade receptacles 24 with relative ease. The blade receptacles 24 may optionally include telescoping means (not shown) for extending the length of the blade receptacles 24. The blade receptacles also preferably include an angled distal portion 25 for reducing the profile of the blade retractor in the vicinity of the surgical area, and thus providing better access and viewing by the surgeon and assistants. In addition, the blades 28 can incorporate a variety of features, as discussed below.

As noted above and as illustrated in FIGS. 1-3, the blade receptacles 24 each preferably include a slot 26 for receiving a blade 28. The slot 26 is shaped to receive a connecting portion 30 of a blade extension 32 that is connected to a blade face 34. The blade extension 32 assists in providing a means of maintaining the bulk of the retractor 10 away from the blades 28. This allows the surgeon to more easily access the surgical wound with the retractor 10 in use. More particularly, the blade extensions 32 of the retractor 10 extend out transversely from the blades 28 so that the bulk of the retractor 10 is maintained away from the incision, thereby allowing improved visualization and access to the surgical wound. In the present invention, the only portion of the retractor 10 that is at the top of the surgical wound is the top of the blades 28 themselves. In accordance with embodiments of the present invention, this results in about 3 mm of coverage on either side of the surgical wound, with the bulk of the retractor 10 positioned well away from the surgical wound. Accordingly, the present invention provides a retractor 10 with interchangeable blade capability that provides relatively long and skinny arms comprising the blade extensions 32 and blade arms 18, thereby placing the bulk of retractor away 10 from the surgical wound. Thus, if during a surgery a surgeon has a retractor 10 in place and the pedicle screws (not shown) have already been inserted into one or more vertebra during the surgery, and the surgeon then desires to subsequently tighten the pedicle screws, then the surgeon can readily access the pedicle screws with the retractor in place. Therefore, the retractor 10 of the present invention provides minimum or low profile access to the surgical wound, resulting in less tissue displacement and/or easier access by the surgeon to the surgical wound.

The slot 26 preferably includes a shape complementary of at least a portion of the connecting portion 30 of the blade extension 32. For example, as best shown in FIG. 2, the connecting portion 30 of the blade extension 32 preferably includes a taller exterior panel 36 that is interconnected to a relatively shorter interior panel 38. In addition, the blade extensions 32 may optionally include telescoping means (not shown) for extending the length of the blade extensions 32.

The connecting portion 30 preferably slides into slot 26 of the blade receptacle 24, where the slot 26, as shown in FIG. 2A, preferably includes a substantially sideways T-shaped cross-section 40 having a taller portion 42 for receiving the exterior panel 36 of the connecting portion 30, and a shorter portion 44 for receiving the interior panel 38 of the connecting portion 30. This preferable geometry restricts rotation of the blades 28 within the bade receptacles 24 during use.

The shape of the slot 26 may take a variety of different cross sections, and the T-shaped cross-section 40 is one possible configuration. The illustrated example of the connecting portion 30 and the slots 26 of the blade receptacles 24 shown in FIGS. 1-3 is one possible configuration for interconnecting the blades 28 to the handle structure of the retractor. However, although not shown, the connecting portion 30 of the blade extensions 32 may snap or otherwise lock into place within the slot 26. For example, the slot 26 and the connecting portion 30 may include detents (not shown), a set screw (not shown), or other means for temporarily locking or securing the connecting portion 30 of the blades 28 into the slots 26.

The blade arms 18 are preferably interconnected to the blade receptacles 24 by a pin 46 that allows the blade receptacle to rotate relative to the blade arm 18. Thus, as the blade arms 18 are spread apart and the blades 28 are separated, the blade receptacles are allowed to rotate.

The front portion 12 further includes two opposing rotatable members 48, wherein the rotatable members 48 further assist in maintaining the preferred orientation of the blade receptacles 24, and thus the blades 28. Each rotatable member 48 has a forward end 50 that preferably is interconnected, such as by a hinge or pin 52, to a rear portion 54 of the blade receptacle 24. The forward end 50 of the rotatable member 48 and the rear portion 54 of the blade receptacles 24 preferably include a pin aperture 56 to accommodate the pin 52.

The rear portion of the rotatable members 48 are preferably operatively connected at a junction 58. For the embodiment shown in FIG. 3, a first rotatable junction member 60a cooperates with a second rotatable junction member 60b, preferably using a screw or pin 62, such that the two rotatable members 48 can rotate relative to each other.

The opposing handle arms 20 are oriented in an angled orientation relative to the forward positioned blade arms 18. More particularly, for either the right or left side of the retractor 10, the handle arm 20 of the handle portion 16 forms a side angle θ with the blade arm 18 of the front portion 12. For the preferred embodiment shown in FIGS. 1-3, the handle arms 20 are cast or otherwise manufactured as one continuous piece with its corresponding blade arm 18. However, the handle arm 20 may be joined to its corresponding blade arm 18 by other means for connecting, such as welding, a bolt, a screw, friction fit, etc., that provides a substantially fixed connection.

The side angle θ between the blade arm 18 and its handle arm 20 is preferably large enough to provide proper and sufficient separation of the blades 28 when the handle arms 20 are moved together. The smaller the side angle θ, the larger the blade separation and vice versa. For posterior spinal surgery where the surgeon desires to retract tissue for access to the spine, the side angle θ is preferably between about 90 and 180 degrees, and more preferably between about 120 and 160 degrees, and more preferably yet between about 130 and 150 degrees, and still more preferably yet, about 145 degrees.

As an example, and without the intent to limit the scope of the invention, one possible configuration is the preferred embodiment where the side angle θ equals about 145 degrees. For this example, the handle arms 20 are each oriented at an offset angle Δ about 35 degrees laterally from alignment along the longitudinal axis L-L of the retractor. Accordingly, when the handle arms 20 are squeezed together, each handle arm 20 traverses a 35 degree arc, and the blade arms 18 are separated. For this example, the separated blade arms 18 form a separation angle φ of about 70 degrees. If the side angle θ is different than 145 degrees, or if the handle arms 20 are not fully closed togther and adjacent each other, then the blade arms 18 will not be fully separated to a separation angle of about 70 degrees. Various side angle θ configurations are within the scope of the present invention, and are encompassed by this description.

Preferably, a central arm 64 substantially aligned along the longitudinal axis L-L is operatively associated with the central hinge 14, as well as the blade arms 18, the handle arms 20, and the rotatable members 48. More particularly, a forward area 66 of the central arm 64 is interconnected to the central hinge 14, and is substantially aligned parallel to the blade arms 18 when the blades 28 are in a closed or adjacent position. The forward area 66 of the central arm 64 preferably includes the position of the central hinge 14 that interconnects the right side of the retractor 10 with the left side of the retractor 10, where the right side of the retractor 10 is substantially the mirror image of the left side of the retractor. The central hinge 14 acts as the pivot point for the front portion 12 and handle portion 16 of the retractor.

To the rear of the central hinge 14 is the junction 58 wherein the first rotatable junction member 60a cooperates with the second rotatable junction member 60b, preferably using a pin 62 that also passes through the central arm 64. Thus, the rear portions of the rotatable members 48 pivot around the pin 62 that interconnects the rotatable members 48 to the central arm 64.

In a separate aspect of the invention, means for locking the position of the retractor blades is provided. As best seen in FIG. 1, each of the handle arms 20 preferably includes a tie arm 68 that further links the handle arms 20 to the central arm 64. A first end 70 of the tie arms 68 are positioned along the length of the handle arms 20 by a tie arm pin 72 that allows the tie arm 68 to rotate or pivot relative to the handle arms 20. A rear portion 74 of the central arm 64 preferably includes an aperture 76 through which a bolt or screw 78 is extended. The screw 78 preferably extends through a second end 80 of each of the tie arms 68, as well as through the central arm 64, where a nut or tightening wheel 82 is threaded onto the screw 78. The tightening wheel 82 can be advanced on the screw 78 to secure the position of the blades 28 in fully closed position, in a fully open position, or at any angle selected between the fully closed or fully open positions. Since the angle of the tie arms 68 will change when moving the blades 28 from a fully closed to fully open position, the slot-like aperture 76 allows the screw 78 to traverse along a portion of the length of the central arm 64. FIG. 1 illustrates the blades 28 in a fully closed position, where the screw 78 and the tightening wheel 82 are in a forward position within the aperture 76. In contrast, FIG. 2 illustrates the blades 28 in a fully open position, where the screw 78 and the tightening wheel 82 are in a rearward position within the aperture 76. An opening or indentation 84 may be provided along the interior of the handle arms 20 to provide room for the screw 78 when the blades 28 are in a fully closed position.

In a separate aspect of the invention, means for interconnecting the position of the retractor 10 to a mechanical arm (not shown) is provided. More particularly, a person such as a surgeon using the retractor 10 may encounter a situation wherein it is desirable to lock or secure the retractor 10 to a separate device or stand, so that the surgeon or an assistant is not required to hold the retractor 10. Accordingly, the retractor 10 of the present invention may be fitted with an adapter 86 for providing such mechanical arm interconnection.

Referring now to FIG. 3, the adapter 86 preferably includes a ball and socket configuration. In a preferred embodiment, the ball portion 88 includes a threaded shaft 90 that is extended through at least a partially spherical region 91 of a socket member 92. The base 93 of the socket member 92 may be threaded onto or otherwise secured to the pin 62 located at junction 58. In addition, the adapter 86 preferably includes a socket shroud 94 that is placed over the socket member 92. The socket shroud 94 preferably includes at least a partially rounded interior surface 95a for rotating against an exterior rounded surface 95b of the socket member 92. Connected to the socket shroud 94 is a mechanical arm connector 96 that can be used to interconnect the retractor 10 to a mechanical arm (not shown). The mechanical arm connector 96 preferably includes means for receiving a mechanical arm, wherein the means for receiving may preferably include a slot 98. In use, the slot 98 can be used in conjunction with a bolt or screw and a plate or nut (not shown), whereby the mechanical arm can be selectively positioned along the mechanical arm connector 96 and tightened as desired.

The threaded shaft 90 has a sufficient length to pass through the upper section of the spherical region 91 of the socket member 92, as well as the socket shroud 94. Preferably, a nut or a tightening wheel 100 is used to tighten the socket shroud 94 over the socket member 92 and the ball portion 88. In use, the tightening wheel 100 can be loosely positioned while the orientation of the retractor 10 is adjusted in combination with securing the mechanical arm connector 96 to the mechanical arm (not shown). The positioning of the mechanical arm connector 96 is aided by the ball portion 88, socket member 92, and socket shroud 94 because the socket shroud 94 can be rotated over the socket member 92 and ball portion 88. That is, the ball portion 88 and its threaded shaft 90 can rotate within the spherical region 91, and the socket shroud 94 can correspondingly rotate over the exterior rounded surface 95b of the socket member 92. Thus, adjustment of interconnecting the retractor 10 to a mechanical arm is relatively easy. Subsequent to orienting the retractor 10 and its mechanical arm connector 96, the tightening wheel 100 can be advanced to tighten and secure the orientation of the retractor 10 to the mechanical arm.

The blades 28 may include a number of structures to assist with insertion and tissue retention. FIG. 1A is a cross section of a preferred embodiment of the blades 28. The blades 28 preferably include a tapered shape from the blade top 102 to their distal tip 104. More particularly, the distal tip 104 of the blades 28 is preferably thinner than the blade top 102. This feature allows for minimizing tissue damage while inserting the blades 28. In addition, the blades preferably include a rounded outwardly facing projection 106. As shown in FIG. 1, the projection 106 may be limited to the forward and rear portions of the distal tip 104 of the blade 28; alternatively, the projection may extend along the entire length of the blade 28. The projections 106 provide a lip for holding and retracting tissue that is located adjacent the interior surgical site, such as tissue adjacent a vertebra of the spine. The blades 28 may also include a tip indentation 108 that allows the distal tip 104 of the blades 28 to be positioned directly over a bone structure, such as an articular process, and then opened to retract tissue in the immediate vicinity of the bone.

The blades 28 may also have a shape wherein a first blade interlocks (not shown) with a second blade while in the closed position. For example, the blades may comprise rounded tipped tines that intermesh in the closed position. In addition, the blade faces 34 of the blades 28 may include a telescoping adjustability, wherein the height of the blades can be easily adjusted at the time of surgery.

In use, a surgeon inserts the retractor blades 28 into tissue while the blades 28 are in a first or closed position. The surgeon then squeezes the handle arms 20 together using the handle openings 22, thereby separating the blades 28 to a second or open position. During the process of opening the blades 28, the structure of the rotatable arms 48, the blade receptacles 24, and the blade arms 18 maintains the blades 28 in an alignment that is substantially parallel to the central arm 64 and longitudinal axis L-L of the retractor 10. Depending upon the amount of retraction desired, the surgeon can partially open the blades or fully open the blades. After the desired amount of retraction is reached, the surgeon can lock the blades 28 in the open position by turning the tightening wheel 82 that is interconnected to the central arm 64 and the tie arms 70. If desired, the retractor 10 can be secured to a mechanical arm by interconnecting the mechanical arm connector 96 of the retractor 10 to the mechanical arm. While securing the retractor 10 to the mechanical arm, the surgeon can adjust the position of the mechanical arm on the retractor 10 by rotating the socket shroud 94 over the socket member 92 and the ball portion 88. After making any such desired adjustments, the surgeon can secure the retractor 10 to the mechanical arm by subsequently tightening the tightening wheel 100.

The insertable and removable characteristic of the blades 28 also allows a surgeon the remove one or both of the blades 28 during an operation, even while the blades are retracting tissue. For example, after the surgeon has inserted the blades into the tissue and retracted the tissue, one or both of the blades can be slid out of the slots 26 of the blade receptacles 24. If desired, the blades can thereafter be interconnected to an alternate retractor handle, or they can be held in place by hand and removed thereafter when desired. In addition, alternate blades can be interchanged into the retractor during the same operation. For example, if the surgeon requires longer blades during a surgery, the first set of blades can be removed and a second set of blades can be quickly and easily inserted into the slots 26 of the blade receptacles 24. Alternatively, if desired, mis-matched blades could purposely be used where a first blade has different characteristics than a second blade, such as a different height, length, width, texturing, indentations, projections, and/or curvature. Thus, the insertable, removable, and interchangeable features of the blades 28 of the retractor 10 allow the surgeon considerable ability to adjust blades even during a surgical procedure.

The retractor 10 can also be used for veterinary operations on animals. For veterinary use, the structures of the retractor may be modified in size to accommodate the subject animal. For example, in equine surgery, the retractor may be modified to include a larger blade and a wider blade separation.

All components of the invention described herein are manufactured of a material appropriate for surgical use. For example, the components can be made of stainless steel. However, it is to be understood that other types of materials may also be used, such as titanium or ceramics.

While various embodiments of the present invention have been described in detail, it is apparent that modifications and adaptations of those embodiments will occur to those skilled in the art. However, it is to be expressly understood that such modifications and adaptations are within the spirit and scope of the present invention.

What is claimed is:

1. A retractor comprising:
    a first handle arm connected to a first blade arm, and a second handle arm connected to a second blade arm;
    a central hinge interconnecting said first blade arm to said second blade arm;
    a first blade receptacle interconnected to said first blade arm at a first blade attachment point, wherein said first blade receptacle pivots relative to said first blade arm, and wherein said first blade receptacle is adapted to receive a first blade;
    a second blade receptacle interconnected to said second blade arm at a second blade attachment point, wherein said second blade receptacle pivots relative to said second blade arm, and wherein said second blade receptacle is adapted to receive a second blade;
    a central arm interconnected to said central hinge, said central arm substantially aligned along a longitudinal axis of the retractor;
    a first rotatable member interconnected to said first blade receptacle at a first rotatable member attachment point and to said central arm at a junction, said junction and said hinge being disposed at different points along said central arm; and
    a second rotatable member interconnected to said second blade receptacle at a second rotatable member attachment point and to said central arm at said junction;
    wherein said first and said second rotatable members maintain the first and second blades substantially parallel to the longitudinal axis of the retractor during opening and closing the first and second blades.

2. The retractor as claimed in claim 1, wherein blades of alternate dimensions are interchangeable with said first and second blade receptacles.

3. The retractor as claimed in claim 1, wherein said first blade is detachable from said retractor and includes a first blade extension which is adapted to be received in the first blade receptacle, and wherein said second blade is detachable from said retractor and includes a second blade extension which is adapted to be received in the second blade receptacle.

4. The retractor as claimed in claim 3, wherein said first and second blade extensions are substantially parallel to the longitudinal axis of the retractor.

5. The retractor as claimed in claim 3, wherein said first and second blade extensions are oriented transverse to a blade face of at least one of said first and second blades.

6. The retractor as claimed in claim 5, wherein said first and second blade extensions with said first and second blades are interchangeable within said first and second blade receptacles.

7. The retractor as claimed in claim 5, wherein only the first and second blades are located within or above an incision, and a remaining portion of the retractor is located transversely from the incision.

8. The retractor as claimed in claim 3, wherein the first and second blades are extended from the retractor, with a minimum profile at the surgical wound.

9. The retractor as claimed in claim 1, wherein during said opening and closing, a first linear distance between said first blade attachment point and said first rotatable member attachment point remains constant, and a second linear distance between said second blade attachment point and said second rotatable member attachment point remains constant.

10. The retractor as claimed in claim 3, wherein the first and second blade extensions each include an exterior panel and an interior panel, the exterior panel being larger than the interior panel, the exterior and interior panel together having a substantially sideways-T shape in cross-section.

11. The retractor as claimed in claim 10, wherein the first and second blade receptacles include a cavity having a substantially sideways-T shape in cross-section, which is adapted to receive the substantially sideways-T shape of the blade extensions.

12. The retractor as claimed in claim 5, wherein a distal tip of the blade face is thinner than a top of the blade face.

13. The retractor as claimed in claim 12, wherein the blade includes a rounded outwardly facing projection.

14. The retractor as claimed in claim 13, wherein the rounded outwardly facing projection is limited to the forward and rear portions of the distal tip.

\* \* \* \* \*